United States Patent
Visinoni et al.

(10) Patent No.: US 10,109,376 B2
(45) Date of Patent: Oct. 23, 2018

(54) MEASURING APPARATUS

(71) Applicant: MILESTONE S.r.l., Sorisole (BG) (IT)

(72) Inventors: Francesco Visinoni, Mozzo (IT);
Matteo Minuti, Brignano Gera d'Adda (IT); Michele Martinelli, Brembate (IT)

(73) Assignee: Milestone S.r.l., Sorisole (BG) (IT)

( * ) Notice: Subject to any disclaimer, the term of this patent is extended or adjusted under 35 U.S.C. 154(b) by 0 days.

(21) Appl. No.: 15/489,999

(22) Filed: Apr. 18, 2017

(65) Prior Publication Data

US 2018/0173851 A1     Jun. 21, 2018

(30) Foreign Application Priority Data

Dec. 21, 2016   (EP) ..................................... 16205706

(51) Int. Cl.
   *G06F 19/00*        (2018.01)
   *G16H 40/20*        (2018.01)
   (Continued)

(52) U.S. Cl.
CPC .............. *G16H 40/20* (2018.01); *G01B 11/00* (2013.01); *G01N 1/31* (2013.01); *G01N 1/312* (2013.01); *G01N 33/4833* (2013.01); *G01N 35/00732* (2013.01); *G06K 7/10722* (2013.01); *G06K 7/10861* (2013.01); *G06Q 10/087* (2013.01);
(Continued)

(58) Field of Classification Search
CPC ...... G02B 21/34; G02B 21/365; G01N 1/312; G01N 2035/00138; G01N 2035/00752; G01N 33/5005; G01N 33/56966; G01N 35/00029; G01N 35/00732; G01N 33/4833; G01N 1/31; G01N 2001/315; G01N 2035/00742; G01N 2035/00821;
(Continued)

(56) References Cited

U.S. PATENT DOCUMENTS 5,526,258 A * 6/1996 Bacus ...................... G06T 7/60
                                                   356/39
5,690,892 A * 11/1997 Babler ............. G01N 35/00029
                                                  422/536

(Continued)

FOREIGN PATENT DOCUMENTS

EP              0592997 A2     4/1994

OTHER PUBLICATIONS

Extended European Search Report issued in connection with the corresponding European Patent Application No. 16205706.1 dated Jul. 11, 2017.

*Primary Examiner* — Claude J Brown
(74) *Attorney, Agent, or Firm* — The H. T. Than Law Group (57) ABSTRACT

Measuring apparatus (1) for tracking human and/or animal tissues comprising: a working area (2) for receiving a tissue; a detecting unit (5) configured to detect a unique tissue code provided with the tissue placed on the working area (2); a measuring unit (9) configured to automatically measure quantitative properties of the tissue placed on the working area (2); and a processing and storing unit (22) configured to automatically link the quantitative properties with the tissue code and to automatically store the so linked quantitative properties and tissue code such that the quantitative properties can be retrieved based on the tissue code.

23 Claims, 4 Drawing Sheets

(51) Int. Cl.
| | |
|---|---|
| *G06K 7/10* | (2006.01) |
| *G06Q 10/08* | (2012.01) |
| *G01N 35/00* | (2006.01) |
| *G01B 11/00* | (2006.01) |
| *G01N 33/483* | (2006.01) |
| *G01N 1/31* | (2006.01) |
| *G01N 33/50* | (2006.01) |
| *G01N 33/569* | (2006.01) |

(52) U.S. Cl.
CPC ... *G01N 33/5005* (2013.01); *G01N 33/56966* (2013.01); *G01N 2001/315* (2013.01); *G01N 2035/00138* (2013.01); *G01N 2035/00742* (2013.01); *G01N 2035/00752* (2013.01); *G01N 2035/00821* (2013.01)

(58) Field of Classification Search
CPC ............... G16H 40/20; G06K 7/10861; G06K 7/10722; G01B 11/00

USPC ........................................................ 235/385
See application file for complete search history.

(56) References Cited

U.S. PATENT DOCUMENTS

| | | | |
|---|---|---|---|
| 5,963,368 A | 10/1999 | Domanik et al. | |
| 8,315,445 B2* | 11/2012 | Sorenson | G01N 35/00732 356/39 |
| 9,691,043 B2* | 6/2017 | Gurney | G06Q 10/063114 |
| 2008/0318265 A1 | 12/2008 | Visinoni | |
| 2010/0007727 A1 | 1/2010 | Torre-Bueno | |
| 2010/0101339 A1* | 4/2010 | Tatsutani | G01N 35/00584 73/863.91 |
| 2013/0224088 A1* | 8/2013 | Britz | B41J 3/407 422/554 |
| 2014/0314623 A1* | 10/2014 | Yamagata | G01N 35/026 422/63 |
| 2015/0211964 A1 | 7/2015 | Stocker et al. | |

* cited by examiner

MEASURING APPARATUS

1. FIELD OF THE INVENTION

The present invention relates to a measuring apparatus, a measuring system and a method for tracking human and/or animal tissues.

2. TECHNICAL BACKGROUND

It is well known in the prior art to collect tissues, tissue samples and/or specimens, e.g. taken at a hospital which is then transferred to a laboratory or the like for histological examination. For a histological examination of human or animal tissues, the tissues are collected from the patients by the clinician in ambulatory environment (biopsies), or by surgeons during operation, then are placed in suitable carriers such as a container, typically filled with fixative such as formalin and sent to the histology laboratory for final examination.

As the tissue is received in the histology laboratory, the first operation performed by the histotechnicians are the accessioning and grossing.

The accessioning consists of a registration of the incoming tissues and insertion of the data in the laboratory information system (LIS). In this phase, a unique tissue code is assigned to the specimen. More specifically, tissues are received, sorted, labelled with barcoded labels (e.g., a barcode label on a carrier such as a container or cassette, in which the tissues are already received and/or in which the tissues will be placed) and related data are manually entered into a Laboratory Information System. The data includes, e.g., patient name, required examination and/or type of sample (e.g., organ name). Moreover, it is known that the recognition of number and size of the respective specimens is also done manually and the information is recorded via a voice recorder or hand-typed via a computer. These information must then be transferred into electronical data which is quite costly. Moreover, during further processing tissues can get lost out of the respective carrier, which cannot be determined or realized during processing, since no data about the respective tissue in the corresponding carrier is stored.

During the following grossing step, the tissue is removed from the carrier, e.g., a transportation container, and reduced in a way that is suitable for the next processes. The reduced tissue or specimen is placed inside a carrier. The reduced specimen must be small enough to be contained inside the carrier, which is, e.g., a standard histological cassette. It means that usually the tissue or specimen is about 0.5 to 5 mm thick, about 0.5 to 20 mm large and 0.5 to 40 mm long. Some tissues, such as small biopsies, are usually already small enough so that the reduction is not required. A polymer foam can be used inside the carrier if the tissue is small, to facilitate the positioning and to avoid an accidental loss of the tissue through the carrier, in particular, cassette slots. Several pieces of tissues of the same patient can be put together in the same carrier. After the preparation, the carrier is usually grouped together with several other carriers inside a rack or rack container. A rack may hold from few tens to few hundreds of carriers. The rack is then used to process several carriers together at the same time inside a tissue processor. The group of several carriers inside a rack is usually named "batch". Even though the rack might be somehow identifiable via a corresponding code, there is no link between the detected rack and the tissues being stored therein. Hence, even if the processing information of the corresponding rack is known, this information cannot be linked with the respective tissues, i.e., the histological samples being carried by the respective carriers.

In a next step, processing is started. Therefore, the rack is provided in a corresponding processing device where—in a first step—the tissues are fixed by use of fixative solution (e.g. formalin). Then—in a second step—the tissues are dehydrated by use of dehydration reagent (e.g. ethanol). In a third step, the tissues are cleared by use of clearing reagent (e.g. isoporpanol or xylene). In a fourth step, the tissues are impregnated (or infiltrated) by use of paraffin wax.

The embedding—which is not commonly considered part of the processing and is an operation usually done outside the tissue processor—is usually done manually or, less commonly, with an automated embedder. The embedding step is required to completely fill the carrier and the impregnated tissue with paraffin wax, creating a solid block.

Afterwards, the block is cut and the slides are prepared and finally put under a microscope for corresponding analysis.

In summary, the previously described steps, in particular the tissue cutting and the tissue (carrier) preparation—are manual steps and thus they are critical for the reliability and traceability of the whole diagnosis process. In particular, in the prior art does not exist an automatic way to:

measure the size of the tissue (in particular, length, width, thickness, area and volume). In the prior art, only a thickness may be measured according to EP2009419B1;

count the tissues inside the cassette; and give an evidence (composite picture) of how the carrier looks like at the end of preparation;

The size of the tissue is important to define precisely the right protocol to be used to process the specimen in a tissue processor. Having the evidence of the number of tissues inside a carrier is important to be able to check the carrier during the (wax) embedding step: Sometimes it happens that one or more tissues of one carrier are lost between the tissue preparation step and wax embedding step. In the prior art does not exist a way to identify this issue. Instead knowing the number of tissues during the sample preparation allows to identify the problem at the following steps.

Furthermore, in the prior art does not exist a way to automatically collect and document that information in an effective and reliable way within a reasonable timeframe: for instance, the expected time to prepare a carrier with small biopsies is usually less than 90 seconds.

In the prior art does not exist a way to automatically track which tissues, i.e., in particular tissue carriers, were put together in a rack forming a batch at the same time when the carrier is prepared with the tissue and the rack is composed. The documentation generated from the tissue processor is usually referred to a batch. Knowing which tissues were put together in the same rack forming a batch is important to allow linking the batch documentation generated from the tissue processor to each cassette of the batch.

Otherwise, the documentation of tissue processor refers to a batch with unknown cassettes.

Moreover, the time of the process executed by the tissue processors depends on the size of the tissues to be processed. Knowing which tissues were put together in the same rack forming a batch and knowing the size of the tissues inside each cassette of the batch allows selecting the proper process for the tissue processor. In the prior art does not exist a way to recognize the right process of tissue processor based on the real size of the batch's tissues to be treated: the user of tissue processor selects a process based on guessing about size of tissues.

It is thus now an object of the present invention to provide a corresponding apparatus, system and method which overcome the aforementioned drawbacks. It is, in particular, an object of the present invention to provide a corresponding device, system and method which allows tracking of the respective tissues during the whole process, particularly with respect to number and dimension (size) of the respective tissues. This is particularly relevant since the correct tissue processing mainly depends on the type and dimension of the respective tissues.

3. SUMMARY OF THE INVENTION

According to the invention, a measuring apparatus for tracking human and/or animal tissues comprises: a working area for receiving a tissue; a detecting means configured to detect a unique tissue code provided in relation to or with the tissue placed on the working area; a measuring means configured to automatically measure quantitative properties of the tissue placed on the working area, preferably (immediately) after or once being detected by the detection means; and a processing and storing unit, i.e., processing and storing means, configured to automatically link the quantitative properties with the tissue code and to automatically store the so linked quantitative properties and tissue code such that the quantitative properties can be retrieved based on the tissue code.

In the context of the present invention, the term "tracking" is preferably to be understood as retrieving information about an object, in particular information regarding the properties and the history of the object, on the basis of an input. Preferably, "tracking" also includes matching, checking and/or reporting.

In the context of the present invention, the term "tissue" is preferably to be understood as a tissue in the field of biology. Preferably, the term "tissue" encompasses tissues ranging from a fraction of an organ, i.e. a tissue sample or specimen, to a complete organ. The term "organ" is not limiting and may refer to any type of organ such as a liver, a kidney etc.

In the context of the present invention, the term "code" is preferably to be understood as representing information and/or a link for information in a way that can be electronically determined or read. The term "tissue" in relation to the term "code" (i.e. "tissue code") preferably relates to basic information, or to a link to basic information, about the tissue, i.e., in particular, information about the tissue that cannot be electronically measured such as name of the organ, name of the patient and/or date of tissue excision. The term "code provided with . . . " or "code provided in relation to . . . " is preferably to be understood as the code being provided along with the respective object (e.g. tissue or rack or the like), i.e. as a separate code, or the tissue (or other object) itself forming (part of) the code, i.e. due to its contours, dimensions, color and the like which can, for instance, be retrieved by way of a picture of this object.

In the context of the present invention, the term "quantitative properties" is preferably to be understood as properties, which can be expressed by means of numbers. In particular, the "quantitative properties" may also be converted in a form (e.g., a code) such that they can be electronically read.

In other words, the present invention particularly provides means that makes it possible to automatically measure and store quantitative properties of the tissue having a defined tissue code, and to retrieve the quantitative properties based on the tissue code. Thus, the whole process, i.e., in particular, the determination of the quantitative properties as well as the retrieval of the quantitative properties for a particular tissue, becomes more efficient and reliable. In particular, equipment for manually measuring and documenting the quantitative properties like, e.g., a voice recorder or the like, can be omitted by means of aforementioned interconnection and configuration. Furthermore, since the quantitative properties are provided in a machine-readable manner and linked with the tissue code, other machines such as a tissue processor may use these information without using any further equipment.

The processing and storing unit may be further configured to restore the relation between the tissue code and the tissue based on the quantitative properties being linked with the tissue code. Thus, if a tissue physically loses its relation to the tissue code, the relation between the tissue code and the tissue may be restored based on the quantitative properties being linked with the tissue code.

The measuring means may be an optical measuring means, preferably a laser scanner, and more preferably configured to measure two- and/or three-dimensional properties of the tissue. The dimensions are preferably to be understood as the dimension of the Euclidean space and with respect to the size and geometry of the tissue. The dimensions may be geometrical features, preferably including length, height and depth. With such a configuration, the optical measuring means provides a means for measuring the quantitative properties of the tissue without being in direct contact (tactile contact) with the tissue.

The measuring means may comprise a moving means, preferably a stepper motor, configured to move the measuring means with respect to the tissue to obtain the quantitative properties of the tissue. Thus, the measuring means may focus on and measure a relatively small area of the tissue such that by moving the measuring means by means of the moving means the small areas are accumulated to obtain the quantitative properties of the sum of the small areas, i.e. of the tissue. Therefore, the space of the measuring means and the measuring apparatus can be further reduced while the measuring apparatus is adapted to measure different sizes of tissues at the same time.

The quantitative properties may include number of tissues and/or geometrical properties of the tissue(s), preferably one-, two- and/or three-dimensional properties, more preferably length, width, thickness, area, and/or volume, even more preferably shape, holes, bulkiness, eccentricity, center, centroid, circularity, rectangularity, roundness, symmetry, compactness, convexity, distance variance, distance standard deviation, distance covariance, distance mean, Euler characteristic, equivalent ellipse, maximum inscribed circle, minimum circumscribed circle, maximum inscribed sphere, minimum circumscribed sphere, sides number, faces number, contour length, orientation, and/or geometric moments.

The processing and storing unit may comprise a data carrier configured to store the linked quantitative properties and tissue code, wherein the data carrier is preferably remotely provided, e.g., as a server.

The first detecting means may be an optical reader, preferably a camera, configured to take a picture of the tissue received by the working area, preferably prior to measuring the quantitative properties of the tissue. Having a picture of the carrier allows further investigation in events of a problem. The picture preferably shows how the tissue and the carrier were at the end of carrier preparation. Based on the picture, it is possible to gain information such as number and position of tissues, color, morphology, foam presence, tissue code, etc. The picture may be later consulted to check for mismatching or errors.

The tissue code may be a one- or two-dimensional barcode, e.g., a matrix-barcode, or may be provided by means of near field technology (NFC), e.g., by means of a RFID chip. By way of the one- or two-dimensional barcode or the near field technology such as the RFID chip a very easy way of providing a link for the information linked with the tissue code is provided. In particular, the one- or two-dimensional barcode or the exemplary RFID chip may be representative of a link providing an address, under which the basic information of the tissue are provided.

The tissue code may be directly connected to the tissue, preferably by means of a tag on the tissue.

The tissue code may be indirectly connected to the tissue, preferably by way of a tissue carrier for carrying the tissue. The tissue carrier may be, e.g., a histological cassette.

Furthermore, the invention relates to a measuring system for tracking human and/or animal tissues. The measuring system comprises: a rack designed to receive at least one human and/or animal tissue, preferably by the (at least one) tissue carrier, for tissue processing; a further detecting means configured to detect a unique rack code (e.g., one- or two-dimensional barcode or near field technology such as an RFID chip) provided in relation to or with the rack, and a previously described measuring apparatus, wherein the processing and storing unit is further configured to automatically link the rack code with the tissue code and, preferably, also with process parameters of tissue processing, and to automatically store the so linked codes, preferably on the data carrier, such that the tissue code(s) and thus the respectively linked quantitative properties can be retrieved based on the rack code. Preferably, also the process parameters of tissue processing—if linked with the code(s)—can be retrieved based on the code(s), i.e. on the tissue code(s) and/or the rack code.

The measuring system allows the tracking of a corresponding tissue and a rack through the whole processing thereof including quantitative properties such as number and dimensions of the tissue. This allows a more accurate histological examination in a more efficient manner. For instance, if a number of tissues are detected with a corresponding problem—i.e. it is derived that the sample was not correctly processed—all the samples which are processed together with the problematic samples in the same rack can be determined and, if necessary, the processing parameters can accordingly be adapted.

Moreover, this configuration does not require the further detecting means to be arranged and positioned such that it can detect the tissue codes for linking the tissue codes with the rack code. Thus, the further detecting means can be arranged and provided with respect to the rack such that it is only facing the rack code. As such, an optimal orientation and arrangement of the further detecting means with respect to the rack can be achieved. Thus, the space of the system can be reduced and the reliability of linking the tissue codes with the rack code can be improved at the same time.

Moreover, since linking of the respective codes is done at the same time when the tissue is prepared, e.g., when the tissue carrier is prepared with the tissue, and the rack is composed, additional steps after the full preparation of the rack, e.g., steps for analyzing the rack, are not required.

The previously described apparatus and/or system may further comprise a user and/or machine interface configured to output the (retrieved) quantitative properties and/or the codes and preferably also the process parameters of tissue processing. As such, the apparatus and/or system can be seamlessly integrated in the histology laboratory environment and the information can be easily and directly displayed to the user.

Furthermore, the present invention relates to a method for tracking human and/or animal tissues. The method comprises the following steps: 1) placing a tissue on a working area, preferably by a tissue carrier carrying the tissue; 2) detecting a unique tissue code provided in relation to or with the tissue by means of a detecting means; 3) automatically measuring of quantitative properties of the tissue by means of a measuring means, preferably (immediately) after or once being detected by the detection means; 4) automatically linking the quantitative properties with the tissue code by means of a processing and storing unit, and 5) automatically storing the so linked quantitative properties and tissue code by means of the processing and storing unit such that the quantitative properties can be retrieved based on the tissue code. Optionally, the relation between the tissue code and the tissue can be restored based on the quantitative properties being linked with the tissue code. In an optional step, the quantitative properties are retrieved based on the tissue code; i.e. by scanning the tissue code and displaying the retrieved information on the user and/or machine interface.

The method may further comprise the following steps: 0) detecting a unique rack code of a rack by means of a further detecting means, 6) placing the tissue on the rack, preferably by the tissue carrier carrying the tissue, 7) automatically linking the tissue code with the rack code by means of the processing and storing unit, and 8) automatically storing the so linked codes, preferably on a data carrier, by way of the processing and storing unit such that the tissue code(s) and thus the respectively linked quantitative properties can be retrieved based on the rack code. Preferably, steps 1 to 8 are repeated for a plurality of tissues such that the tissue codes can be retrieved based on the rack code.

The method may further comprise the step of processing the tissues on the rack. Preferably, processing the tissues comprises the steps of fixation, e.g., by use of a fixative solution such as formalin, dehydration, e.g., by use of a dehydration reagent such as ethanol, clearing, e.g., by use of a clearing agent such as isopropanol and/or xylene, and impregnation and/or infiltration, e.g., by use of paraffin wax.

The method may further comprise the steps of automatically linking process parameters of the tissue processing with the rack code and, preferably, also with the tissue code(s), and of storing the so linked process parameters and code(s) such that the process parameters can be retrieved based on the code(s).

What was said before regarding the apparatus and the system applies likewise to the method of the present invention.

4. DESCRIPTION OF A PREFERRED EMBODIMENT

In the following, the invention is described exemplarily with reference to the enclosed figures, in which

Figure 1:
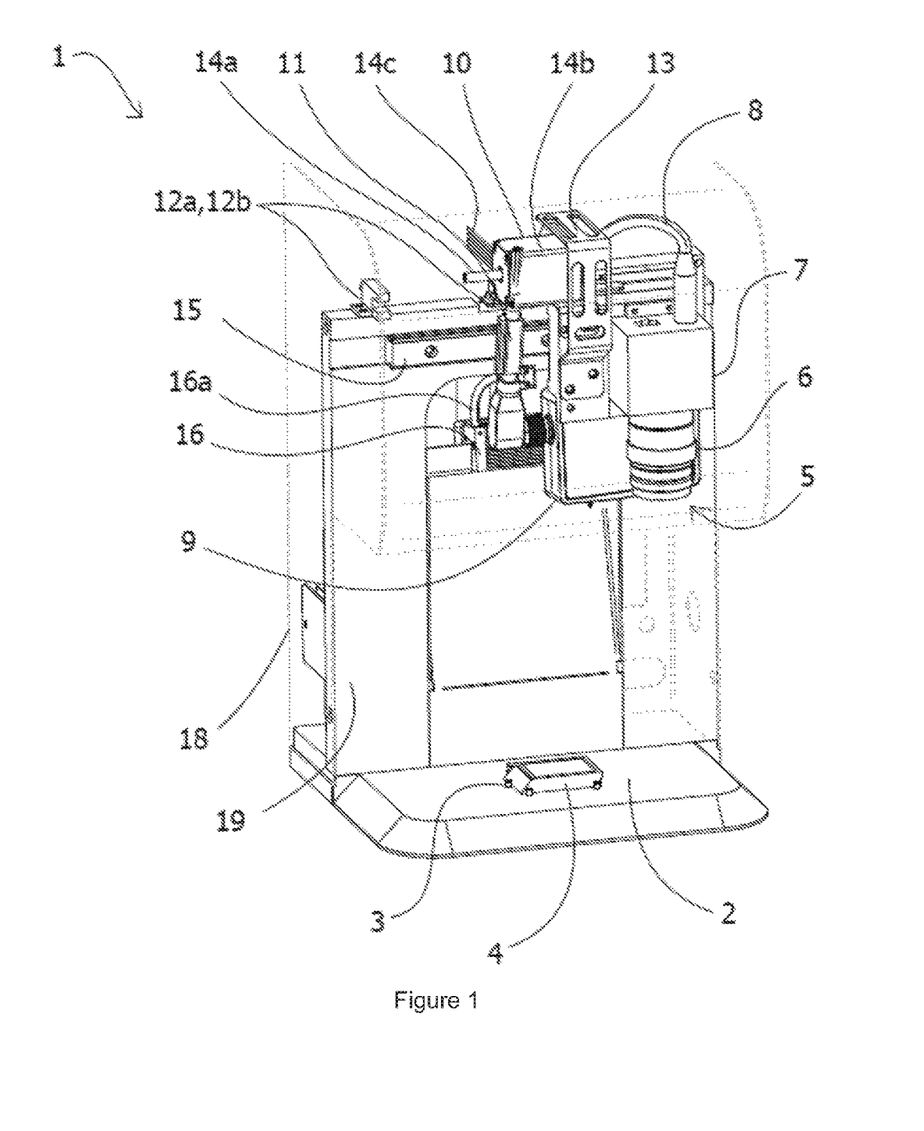
FIG. 1 is a perspective view of a preferred embodiment of the measuring apparatus according to the present invention.
Figure 2:
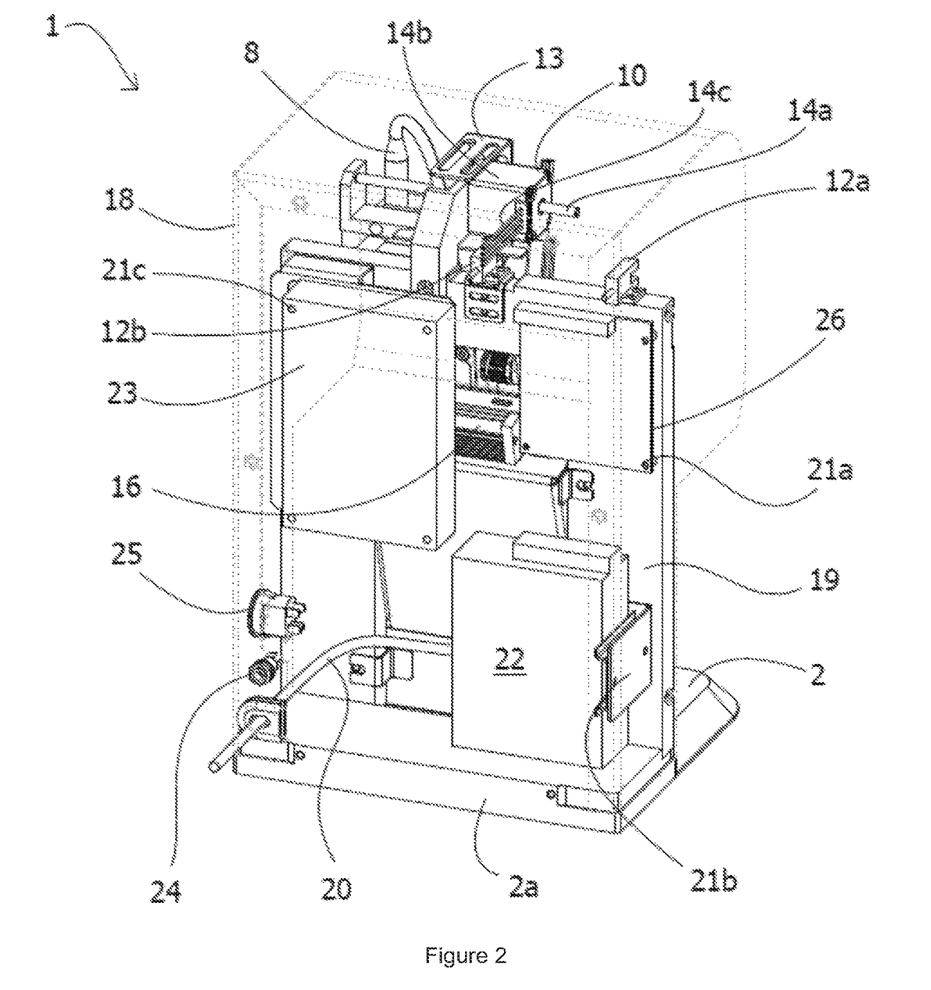
FIG. 2 is a perspective view of the measuring apparatus of FIG. 1.
Figure 3:
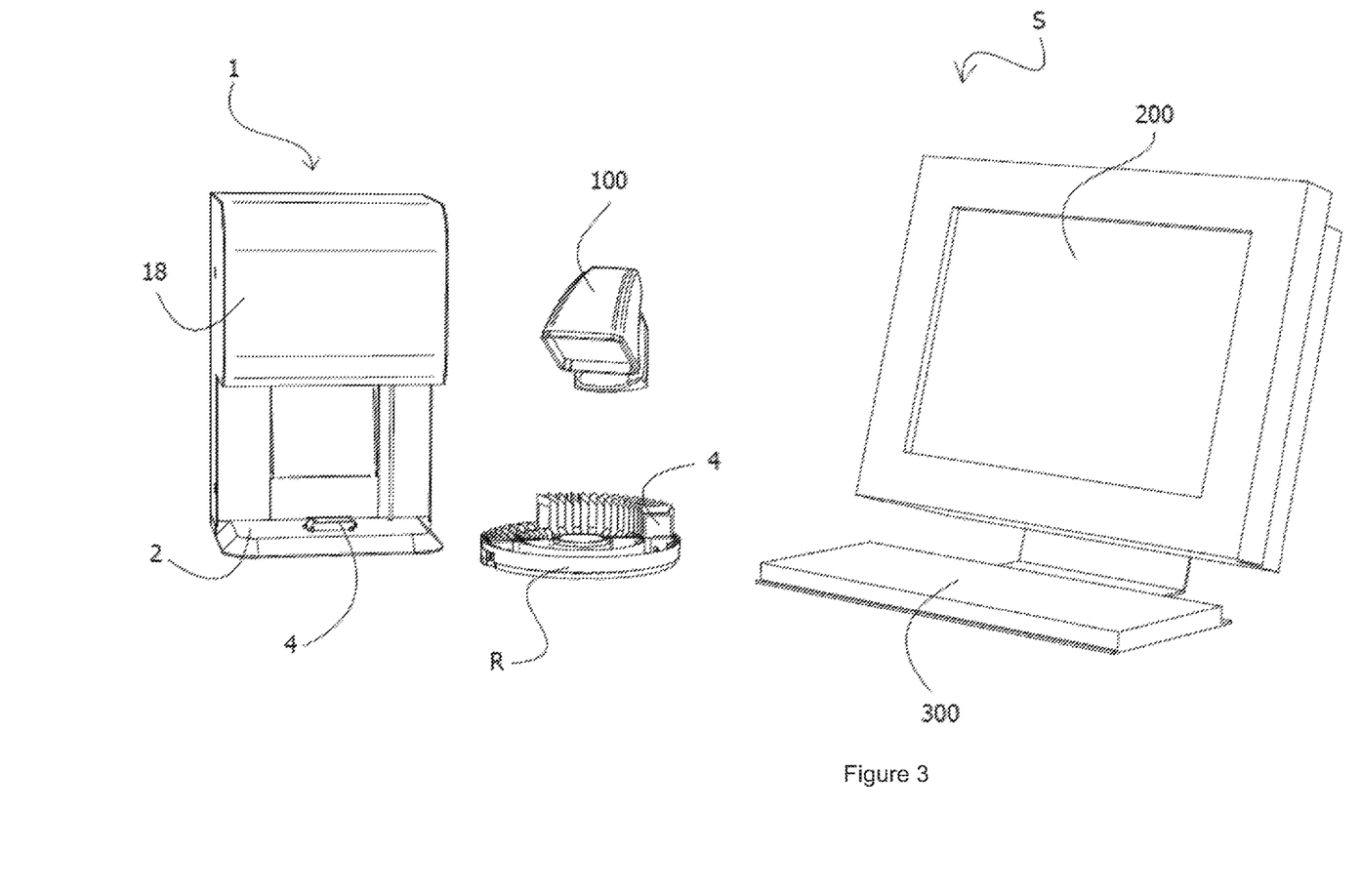
FIG. 3 is a perspective view of a preferred embodiment of the measuring system according to the present invention.

FIGS. 1 to 3 show a preferred embodiment of the measuring apparatus 1 for tracking human and/or animal tissues.

As can be seen in FIGS. 1 to 3, the measuring apparatus 1 comprises a working area 2 for receiving a tissue. The working area 2 may have a substantially flat surface for receiving a tissue. Preferably, the working area 2 has a defined thickness and is, more preferably, at least partially chamfered at its edges such that the working area 2 has a trapezoidal cross-sectional area when viewed perpendicular to the normal vector of the flat surface. The working area 2 may have a contact surface opposite of the flat surface being in contact with another working area, e.g., a table surface or a bench surface of a laboratory bench in a histology laboratory. Preferably, the working area 2, in particular the flat surface, is extending in a width and a length direction, wherein, preferably, the length direction is equal or greater than the width direction. Preferably, the working area 2 comprises a receiving means 3 for receiving a tissue. The receiving means 3 may centrally position the tissue with respect to the working area 2. Furthermore, a counter weight 2a may extend from the working area 2 to the back of the measuring apparatus 1.

The measuring apparatus 1 further comprises a detecting means 5 configured to detect a unique tissue code provided in relation to or with the tissue placed on the working area 2. The detecting means 5 may be configured to automatically detect the presence of the tissue code, preferably being in the vicinity of the working area 2 or on the working area 2. In order to automatically detect the presence of the tissue code in the vicinity of the working area 2 or on the working area 2, the detecting means 5 may permanently observe the working area 2 and, optionally, the surroundings of the working area 2 and evaluate whether or not the tissue code is on the working area 2 or in the vicinity of the working area 2. The automatic detection may be achieved by means of image and/or pattern recognition. The automatic detection may be performed by acquiring images of the working area with the detecting means 5, e.g., with a camera, and processing it with a software able to identify the codes in the image. Preferably, once a tissue with a valid tissue code is placed on the working area 2, the detecting means 5 automatically detects the presence of the tissue code and, thus, the presence of the tissue.

As can be seen in FIGS. 1 and 2, the detecting means 5 may be arranged above the working surface 2 and preferably distanced from the working surface 2. When viewed perpendicular to the working area 2, preferably perpendicular to the flat surface of the working area 2, the detecting means 5 may be arranged at least partially and preferably entirely inside of the working area 2. When viewed in said direction, the detecting means 5 may also be arranged at least partially and preferably entirely inside of a half of the working area 2. The half of the working area 2 may be a half of the working area 2 with respect to the length of the working area 2. The detecting means 5 may have an observation cone, in which the detecting means 5 can detect the tissue code. Said cone preferably has an axis, preferably a symmetrical axis, being perpendicular to the working area 2, preferably perpendicular to the flat surface of the working area 2.

The detection means 5 may be an optical reader, e.g., a barcode scanner or a camera, configured to detect the tissue code. The detection means 5 may also be a near field technology reader such as a RFID reader.

Preferably, there is a physical relationship between the tissue-code and the tissue. As such, the tissue code may be directly or indirectly connected to the tissue. When connecting the tissue-code directly to the tissue, the tissue-code may be connected by means of a tag (not shown) on the tissue. When connecting the tissue code indirectly to the tissue, the tissue code may be connected with the tissue by way of a tissue carrier 4 designed to carry the tissue. The tissue carrier 4 may comprise a housing composed of a base having sidewalls and a lid. Either the lid or the base may comprise the tissue code. Preferably, a sloping side of the tissue carrier 4 comprises the tissue code. More preferably, the tissue carrier 4, in particular the base of the tissue carrier 4, is chamfered or sloped at one sidewall, wherein the chamfered sidewall may comprise the tissue code.

The tissue carrier 4 may be a histological cassette or a container. Preferably, the receiving means 3 of the working area 2 are designed for receiving the tissue carrier 4. The receiving means 3 are preferably designed such that the tissue carrier 4 is fixed in at least two degrees of freedom for translation, preferably the two degrees of freedom for translation of the working area 2, i.e. of the flat surface of the working area 2. The receiving means 3 may comprise protrusions, preferably at least three protrusions, more preferably at least four or five protrusions, for receiving the tissue carrier 4. The protrusions may be provided tangentially at and outside of the perimeter of the tissue carrier 4, preferably of the base of the tissue carrier 4.

As can be seen in FIGS. 1 and 2, the measuring apparatus 1 further comprises a measuring means 9 configured to automatically measure quantitative properties of the tissue placed on the working area 2. The measuring means 9 may be provided above the working area 2 and preferably distanced from the working area 2. When viewed perpendicular to the working area 2, preferably perpendicular to the flat surface of the working area 2, the measuring means 9 may be arranged at least partially and preferably entirely inside of the working area 2. When viewed in said direction, the measuring means 9 may also be arranged at least partially and preferably entirely inside of a half of the working area 2. The half of the working area 2 may be a half of the working area 2 with respect to the width of the working area 2.

The measuring means 9 may be a contactless measuring means such as an optical measuring means, e.g., an optical profile sensor or a non-contact line distance sensor, that uses light to measure the distance between the measuring means 9, preferably a reference point in the measuring means 9, and the tissue, preferably a plurality of points on the surface of the tissue, such that the two- and/or three dimensional shape of the tissue can be obtained. The measuring means 9 can be a laser scanner. Preferably, the measuring means 9 is configured to measure two- and/or three-dimensional properties of the tissue. The measuring means 9 may have a measuring axis, e.g., a beam of the light being used for measuring, wherein the axis is substantially perpendicular to the working area 2. The measuring means 9 may be also a camera that measures quantitative properties of the tissue. For instance, the measuring means 9 being a camera may measure quantitative properties by way of image recognition.

The measuring means 9 may comprise a moving means 10 configured to move the measuring means 9 with respect to the tissue to obtain the quantitative properties of the tissue. The moving means 10 may move the measuring means 9 in a plane substantially parallel to the working area 2, preferably along a linear axis in a direction parallel to the length direction of the working area 2. The moving means 10 may move the measuring means 9 such that the measuring means 9 only needs to focus on a measurement perpendicular to the movement of the moving means 10. Thus, moving the measuring means 9 in a first direction, e.g., in the length direction of the working area 2, and measuring by way of the measuring means perpendicular to the first direction, e.g., in the width direction of the working area 2, accumulates the measurements perpendicular to the first direction to constitute the quantitative properties of the tissue.

The moving means 10 may be more distanced from the working area than the detecting means 5 and/or the measuring means 9. The moving means 10 may be disposed on a side of the detecting means 5 and/or the measuring means 9, the side having a normal vector pointing away from the working area 2.

The moving means 10 may be a motor 14b meshing with an element 14a, e.g., with a gear wheel such as a spindle, to effect the desired movement of the measuring means 9. One of the element 14a or motor 14b may be fixed with respect the working area 2, wherein the other one is fixed with respect to the measuring means 9 being moveable with respect to the working area 2. As shown in FIGS. 1 and 2, the motor 14b may be fixed with respect to the working area 2, wherein the element 14a is fixed with respect to the moveable measuring means 9. The element 14a may penetrate the motor 14b for meshing. The element 14a may be supported by bearings at its ends. Preferably, the motor 14b is a stepper motor.

The moving means 10 may further include position sensors 12a, 12b, wherein, preferably, the sensors 12a, 12b cooperate with an element 14c of the moving means 10. The position sensor 12a, 12b may provide the position and/or velocity of the measuring means 9 with respect to the working area 2, the tissue, respectively. The position and/or velocity provided by the sensor 12a, 12b may be used to obtain the quantitative properties. The sensor 12a, 12b may comprise one or at least two sensors, namely a first sensor 12a and a second sensor 12b. The sensor 12a, 12b may be provided along the moving direction of the measuring means 9, preferably along a direction being parallel to the length direction of the working area 2.

The moving means 10 may further comprise guiding means 15, e.g., a rail, for guiding the measuring means 9, when the measuring means 9 is moved by the moving means 10. The guiding means 15 may extend in a direction being substantially parallel to the length direction of the working area 2.

The quantitative properties measured by the measuring means 9 may include number of tissues and/or geometrical properties of the tissue(s). For instance, the measuring means 9 may be configured such that it can recognize the number of tissues (i.e., number counting) and/or the geometrical properties of the tissue(s) by way of image and/or pattern recognition. The number of tissues may be recognized by the number of recognized closed geometries.

The quantitative properties may include one-, two- and/or three-dimensional properties, in particular with respect to the geometry of the tissue, preferably length, width, thickness, area, and/or volume, more preferably shape, holes, bulkiness, eccentricity, center, centroid, circularity, rectangularity, roundness, symmetry, compactness, convexity, distance variance, distance standard deviation, distance covariance, distance mean, Euler characteristic, equivalent ellipse, maximum inscribed circle, minimum circumscribed circle, maximum inscribed sphere, minimum circumscribed sphere, sides number, faces number, contour length, orientation, and/or geometric moments.

The optical reader of the detecting means 5 or an additional optical reader may be configured to take a picture of the tissue received by the working area 2, wherein, preferably, the picture is taken prior to measuring the quantitative properties by the measuring means 9. The picture may be taken as soon as the detecting means 5 detects a tissue code, preferably a tissue code being received by the working area 2. The optical reader or the additional optical reader may comprise a (digital) camera comprising an optic 6, e.g., a lens, and a processing unit 7 connected with the optic 6.

The measuring apparatus 1 further comprises an input/output electronic control unit 23, a motor control unit 26, and processing and storing unit 22 such as a computer The units 22, 23, 26 may be arranged on a side being opposite to a side, where the working area 2, detecting means 5 and the measuring means 9 are provided. For the reason of space saving, the at least two units 22, 23, 26 may be evenly distributed on their side. Preferably, the units 22, 23, 26 are attached to the side by means of attaching elements 21a, 21b, 21c, e.g., screws and/or angle brackets. The sides may be sides of a middle plate 19 preferably provided as a mounting plate.

The input/output electronic control unit 23 and the motor control unit 26 may be electronically connected with the processing and storing unit 22 providing the right electrical signal interface between the processing and storing unit 22 and a lighting means 16, the sensors 12a, 12b, and the element 14c of the moving means 10.

The processing and storing unit 22 is configured to automatically link the quantitative properties with the tissue code. For this reason, the detecting means 5 and the measuring means 9 may be electronically connected with the processing and storing unit 22 providing the quantitative properties and the tissue code for the processing and storing unit 22. The electronic connection may be achieved by way of a data cable, preferably by way of USB or Ethernet or RS232 or RS485, e.g., by way of the data cables 8, 11 fastened to a cable tray 13. The processing and storing unit 22 may comprise a controller, e.g., a chip, for executing commands for automatically linking the quantitative properties with the tissue code.

The processing and storing unit 22 is configured to automatically store the so linked quantitative properties and tissue code. For said automatically storing, the processing and storing unit 22 may comprise a controller, e.g., a chip, for executing commands for automatically storing. The linked quantitative properties and tissue code may be stored in a machine-readable manner, preferably in a digital format, e.g., a digital format accessible from Tracking Systems or Laboratory Information Systems or other applications. The processing and storing unit 22 may also generate a human-readable report in a digital format, preferably accessible from Tracking Systems or Laboratory Information Systems or other applications for further tracking. The processing and storing unit 22 may comprise a data carrier configured to store the linked quantitative properties and tissue code, preferably in a database on the data carrier. The data carrier may be provided integrally with the measuring apparatus 1, preferably integrally with the processing and storing unit 22, e.g., on a chip or the previously described chips or on a hard disk. The data carrier may also be provided remotely, e.g., as a server. The remote provision may be achieved by means of a wire(less) and/or Ethernet and/or internet connection by way of a data cable 20 or antenna.

The quantitative properties can be retrieved based on the tissue code. For retrieving the quantitative properties, the tissue code may be input by an input device. The input device is preferably an optical reader, e.g., a barcode scanner, configured to detect the tissue code. The input device may be the detecting means 5. Retrieving the tissue code may be performed by an output device. The output device is preferably a computing device having a display for displaying the quantitative properties. The output device and the input device may be integrally provided.

Moreover, the tissue code may be retrieved based on the quantitative properties of the tissue. In particular, this may be used for restoring the relation between the tissue code and the tissue, if the relation between the tissue code and the tissue gets lost, e.g., when the tissue falls out of a tissue carrier carrying the tissue code. For retrieving the tissue code, the quantitative properties of the tissue may be measured by the measuring means 9 or by any other measuring means being connected with the processing and storing unit 22. The processing and storing unit 22 may compare the measured quantitative properties with the stored quantitative properties, each of the quantitative properties being linked with a respective tissue code. The processing and storing unit 22 may then select the tissue code of the stored quantitative properties, which matches best with the measured quantitative properties. The retrieved tissue code may then be output by the aforementioned output device or by another output device such as a tissue code generator, e.g., a barcode printer or a NFC chip generator.

The lighting means 16, e.g., an illuminator, for illuminating the working area 2, may be automatically switched on, e.g., when the detecting means 5 detects a tissue code.

Preferably, the lighting means 16 is connected with the input/output electronic control unit 23, e.g., by a cable 16a, for switching the lighting means 16 as a function of the tissue code. Preferably, the lighting means 16 penetrates the middle plate 19 and is attached thereto. In particular, the lighting means 16 makes the measuring apparatus 1 independent from the room light and its variation.

As can be seen in FIGS. 1 and 2 in dashed lines and in FIG. 3 in continuous lines, the measuring apparatus may comprise a housing or chassis 18 for housing at least the detecting means 5, the measuring means 9, and the units 22, 23, 26. When viewed in a side view of the measuring apparatus 2, preferably in a direction perpendicular to the normal vector of the working area 2, more preferably in the length direction of the working area 2, the housing 18 may comprise a first half and a second half, wherein the first half houses the units 22, 23, 26, and wherein the second half houses the detecting means 5 and the measuring means 9. Preferably, the second half is provided above the working area 2, wherein, more preferably, the second half may be connected with the working area 2 by way of the first half. The housing 18 may have substantial P-profile constituting a substantial C-profile with the working area 2. The second half of the housing 18 and the working area 2 may be provided on a first side of the middle plate 19, wherein the first half of the housing 18 may be provided on a second site of the middle plate 19 being opposite to the first side. The housing 18 may have a footprint dimension comfortable for the use during the tissue preparation, e.g. 200 mm×300 mm.

Referring to FIG. 2, the measuring apparatus 1 may comprise a power supply 24 for powering the respective means. The power supply 24 is preferably provided on the back of the measuring apparatus 1, in particular on the back of the housing 18. Moreover, the measuring apparatus 1 may comprise a main switch 25 for switching the measuring apparatus on or off.

Referring to FIG. 3, a measuring system S comprises a rack R designed to receive at least one human and/or animal tissue. The rack R may be designed to receive at least one, preferably at least two tissues, preferably from tens to hundreds tissues. The rack R may have a structure corresponding to the tissue to be received. The rack R may further have a symmetrical, preferably a cylindrical, structure. The rack R may be designed to receive the tissue by the tissue carrier 4. The rack R may be used for tissue processing.

The measuring system S comprises a further detecting means 100, e.g., an optical reader such as a barcode reader or a near field technology reader such as a RFID reader, configured to detect a unique rack code provided in relation with the rack R. The detecting to means 100 may be provided close, preferably above, the rack R. The detecting means 100 may also be integrated in the detecting means 5. Thus, the detecting means 5 may simultaneously function as the further detecting means 100 or vice versa. The detecting means 100 may be configured to automatically detect the presence of the rack code in the vicinity of the detecting means 100, i.e., a specific rack composing area where the detecting means 100 looks at. In order to automatically detect the presence of the rack code in the vicinity of the detecting means 100, the detecting means 100 may permanently observe the vicinity of the detecting means 100 and evaluate whether or not the rack code is in the vicinity of the detecting means 100. The automatic detection may be achieved by means of image and/or pattern recognition. The rack code may be provided on a surface, preferably on an outer surface, of the rack R.

Furthermore, the measuring system S comprises the aforementioned measuring apparatus 1. The processing and storing unit 22 of the measuring apparatus may be further configured to automatically link the rack code with the tissue code and to automatically store the so linked codes such that the tissue code(s) and thus the respectively linked quantitative properties can be retrieved based on the rack code. The so linked codes may be stored in a machine-readable manner, preferably a digital format accessible from Tracking Systems or Laboratory Information Systems and/or tissue processors and/or other applications. In other words, the measuring apparatus 1 may link the tissue code with the quantitative properties and, furthermore, link the tissue code with the rack code of the rack R. For this configuration, the measuring apparatus 1, in particular the processing and storing unit 22, is preferably physically connected with the further detecting means 100. The processing and storing unit 22 may further be configured such that it can recognize the replacement of a rack, i.e. the replacement of a previous rack, in which the tissues have been previously placed, by a new rack, in which the tissues are to be placed. Thus, if the rack is replaced by another one, the processing and storing unit 22 recognizes the new rack code through the detecting means 100 and then starts to link the tissue code with the new rack code. If no rack code is detected, the measuring apparatus 1 may raise a warning to the user.

A method for tracking human and/or animal tissue may comprise at least the following steps: 1) placing a tissue on the working area 2, preferably by the tissue carrier 4; 2) detecting a unique tissue code provided in relation to or with the tissue by means of the detecting means 5; 3) automatically measuring of quantitative properties of the tissue by means of the measuring means 9; 4) automatically linking the quantitative properties with the tissue code by means of the processing and storing unit 22; and 5) automatically storing the so linked quantitative properties and tissue code by means of the processing and storing unit 22 such that the quantitative properties can be retrieved based on the tissue code. Finally, the quantitative properties can be retrieved based on the tissue code as already described herein above.

Preferably, steps 1) to 5) are performed in an ascending order, taking into account the number of the respective steps, i.e. 1) to 5). However, steps 1) to 5) may also be performed in a different order, as long as the tissue code can be linked with the quantitative properties. For instance, step 3) may also be performed before step 2).

Step 3) is preferably performed after step 2). After detecting the presence of the tissue in step 2), the measuring apparatus 1 may automatically take a picture (step 2) and then may start to measure a three-dimensional scan (step 3): for instance, the moving means 10 moves the measuring means 9 over the tissue from one end to the other. The apparatus 1 may acquire the dimensional data provided by the measuring means 9 during its run. The position of the measuring means 9 may be monitored through the position sensors 12a, 12b and through the moving means 10, e.g., by counting of the rotation steps of the stepper motor. At the end of measuring, the device may get a three-dimensional data representation of the tissue and, preferably, of its contained number of tissues or tissue samples.

Preferably, the method further comprises the following steps: 0) detecting the unique rack code of the rack R by means of the further detecting means 100; 6) placing the tissue on the rack R, preferably by the tissue carrier 4; 7) automatically linking the tissue code with the rack code by means of the processing and storing unit 22; and 8) automatically storing the so linked codes, more preferably on the data carrier, by way of the processing and storing unit 22 such that the tissue code or tissue codes and thus also the respectively linked quantitative properties can be retrieved based on the rack code.

Preferably, step 0) is performed before steps 1) to 8). However, step 0) may also be performed after or during steps 1) to 8). If a plurality of tissues needs to be assigned to the rack R and, thus, the tissue code of each of the plurality of tissues needs to be linked with the rack code, steps 1) to 8) are repeated for the plurality of tissues, i.e., steps 1) to 8) are repeated for each of the plurality of tissues. Preferably, the repetition is automatically terminated, more preferably as soon as the maximum number of tissues, which the rack can receive or carry, has been reached. For instance, the rack code may include the maximum number of tissues, which can be received by the rack R. The repetition may also be manually terminated, e.g., by means of a user input or removing the rack from the rack composing area where the detecting means 100 looks at.

Preferably, the method further comprises the step of tissue processing, i.e. processing the tissues placed on the rack R. Tissue processing may be performed in a processor (not shown). Preferably, processing the tissues, i.e. tissue processing, comprises at least one of the following steps, more preferably all of the following steps:

Fixation, e.g., by use of a fixative solution such as formalin,

Dehydration, e.g., by use of a dehydration reagent such as ethanol,

Clearing, e.g., by use of a clearing agent such as isopropanol and/or xylene,

Impregnation and/or infiltration, e.g., by use of paraffin wax.

Tissue processing may include defined processing parameters, preferably physical parameters (flow rates, pressure, temperature etc.) of processing means, e.g., parameters of the means used in the steps of processing. The processing parameters may be automatically linked with the rack code and, more preferably, also with the tissue code(s). The processing and storing unit 22 may be configured to automatically link the processing parameters with the codes and to automatically store the so linked process parameters and code(s) such that the process parameters can be retrieved based on the code(s). The tissue processor may be configured to monitor the processing parameters and provide the processing parameters for linking with the rack code, preferably for the processing and storing unit 22.

As can be seen in FIG. 3, a user interface 200, 300 may be provided. The user interface 200, 300 may be configured to output the quantitative properties and/or the codes. More specifically, the user interface 200, 300 may output the quantitative properties linked with the tissue code and, preferably, the quantitative properties linked with the tissue code and further linked with the rack code. The user interface 200, 300 may also be configured to input data. The data may comprise the tissue code and/or the rack code. For instance, a user may input the rack code and/or the tissue code in the user interface 200, 300, preferably by means of an input device (e.g., a keyboard) and/or an optical reader (e.g., a barcode scanner). On the basis of these codes, the user interface 200, 300 may then output the linked tissue codes and/or the linked quantitative properties.

The tissue code and the rack code may be a one- or two-dimensional code such as a matrix-barcode, i.e., e.g., a Data Matrix ECC200. The codes may also be a QR code, Micro QR Code, a PDF417, an Aztec Code, etc. The codes, respectively, can also be provided by different means, e.g., by means of near field technology (NFC) such as an RFID-chip.

Figure 4:
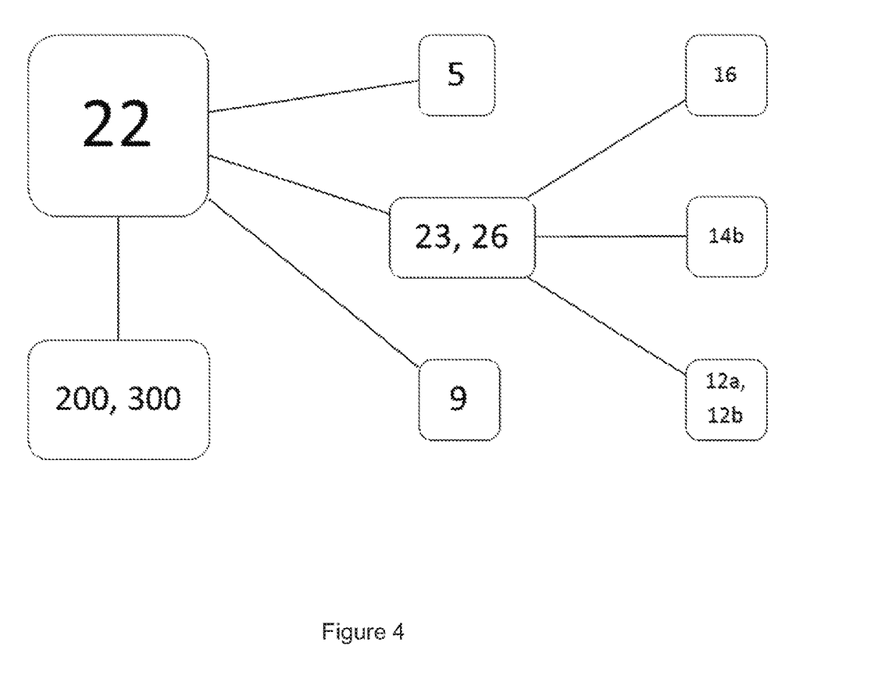
FIG. 4 is a functional diagram of a preferred embodiment of the measuring apparatus according to the present invention.

FIG. 4 shows an exemplary functional diagram, in which the functional connection between the respective means is shown. The moving means 10 (preferably including the sensors 12a, 12b and the motor 14b) and, preferably, the lighting means 16, is/are connected with the input/output electronic control unit 23 and the motor control unit 26, e.g., by way of a data cable. The detecting means 5 and the measuring means 9 may be connected with the processing and storing unit 22, wherein the processing and storing unit 22 is connected with the input/output electronic control unit 23 and the motor control unit 26. The processing and storing unit 22 may also be provided remotely, e.g., by an external computer. The motor control unit 26 may include drivers for driving the measuring means 9 and, preferably, the detecting means 5, by the moving means 10. The processing and storing unit 22 may be connected with the user interface 200, 300. Preferably, the user interface 200, 300 may comprise a display unit 200 and a human machine interface 300 comprising, e.g., a mouse, a keyboard and/or a touchscreen. The display unit 200, preferably the user interface 200, 300, may be embedded in the housing 18 or externally connected.

The processing and storing unit 22 may include algorithms for processing the measured quantitative properties, e.g., data analysis for deriving quantitative properties or indicators, and/or algorithms for image and pattern recognition, e.g., for inspection of the picture taken. Preferably, the processing and storing unit 22 includes a software for image inspection and analysis of the quantitative properties. The software may process 3D data and/or the picture extracting the tissues from the picture and providing the quantitative properties, preferably size and three-dimensional geometry of said tissues (length, width, thickness, area, volume, shape, etc.). Furthermore, the processing and storing unit 22, in particular the software or the algorithms, may be configured to suppress noise, in particular background objects, that do not belong to the tissue (e.g., the carrier such as the cassette or foam provided in the carrier or cassette).

It should be clear to a skilled person that the embodiment shown in the figures are only preferred embodiments, but that, however, also other designs of a measuring apparatus and system can be used.

The invention claimed is:

1. Measuring apparatus (1) for tracking human and/or animal tissues comprising:
    a) a working area (2) for receiving a tissue;
    b) a detecting means (5) configured to detect a unique tissue code provided with the tissue placed on the working area (2);
    c) a measuring means (9) configured to automatically measure quantitative properties, which include three-dimensional properties, of the tissue placed on the working area (2); and
    d) a processing and storing unit (22) configured to automatically link the quantitative properties with the tissue code and to automatically store the so linked quantitative properties and tissue code such that the quantitative properties can be retrieved based on the tissue code.

2. Measuring apparatus (1) according to claim 1, wherein the processing and storing unit (22) is further configured to restore the relation between the tissue code and the tissue based on the quantitative properties being linked with the tissue code.

3. Measuring apparatus (1) according to claim 1, wherein the measuring means (9) is an optical measuring means.

4. Measuring apparatus (1) according to claim 1, wherein the measuring means (9) comprises a moving means (10) configured to move the measuring means (9) with respect to the tissue to obtain the quantitative properties of the tissue.

5. Measuring apparatus (1) according to claim 1, wherein the quantitative properties include number of tissues or the combination thereof.

6. Measuring apparatus (1) according to claim 5, wherein the quantitative properties include length, width, thickness, area, and/or volume, shape, holes, bulkiness, eccentricity, center, centroid, circularity, rectangularity, roundness, symmetry, compactness, convexity, distance variance, distance standard deviation, distance covariance, distance mean, Euler characteristic, equivalent ellipse, maximum inscribed circle, minimum circumscribed circle, maximum inscribed sphere, minimum circumscribed sphere, sides number, faces number, contour length, orientation, or geometric moments or a combination thereof.

7. Measuring apparatus (1) according to claim 1, wherein the processing and storing unit (22) comprises a data carrier configured to store the linked quantitative properties and tissue code.

8. Measuring apparatus (1) according to claim 7, wherein the data carrier is remotely provided as a server.

9. Measuring apparatus (1) according to claim 1, wherein the detecting means (5) is an optical reader configured to take a picture of the tissue received by the working area (2).

10. Measuring apparatus (1) according to claim 1, wherein the tissue code is a one- or two-dimensional barcode or wherein the tissue code is provided by means of near field technology.

11. Measuring apparatus (1) according to claim 1, wherein the tissue code is indirectly connected to the tissue.

12. Measuring apparatus (1) according to claim 11, wherein the tissue code is indirectly connected to the tissue by way of a tissue carrier (4) for carrying the tissue.

13. Measuring system (S) for tracking human and/or animal tissues comprising:
    A. a rack (R) designed to receive at least one human and/or animal tissue for tissue processing;
    B. a further detecting means (100) configured to detect a unique rack code provided with the rack (R); and
    C. a measuring apparatus (1) according to claim 1, wherein the processing and storing unit (22) is further configured to
       automatically link the rack code with the tissue code, and
       to automatically store the so linked codes, such that the tissue code(s) and thus the respectively linked quantitative properties can be retrieved based on, the rack code.

14. Measuring system (S) according to claim 13 further comprising a user and/or machine interface (200, 300) configured to output the quantitative properties and/or the codes.

15. Measuring system (S) according to claim 13, wherein the processing and storing unit (22) is further configured to automatically store the so linked codes, such that the process parameters of tissue processing can be retrieved based on the tissue code(s) and/or the rack code.

16. Measuring apparatus (1) according to claim 1 further comprising a user and/or machine interface (200, 300) configured to output the quantitative properties and/or the codes.

17. Measuring apparatus (1) according to claim 1, wherein the measuring means (9) is configured to measure two- and three-dimensional properties of the tissue.

18. Method for tracking human and/or animal tissues comprising the steps of:
    1) placing a tissue on a working area (2);
    2) detecting a unique tissue code provided with the tissue by means of a detecting means (5);
    3) automatically measuring of quantitative properties of the tissue by means of a measuring means (9), wherein the quantitative properties include three-dimensional properties;
    4) automatically linking the quantitative properties with the tissue code by means of a processing and storing unit (22), and
    5) automatically storing the so linked quantitative properties and tissue code by means of the processing and storing unit (22) such that the quantitative properties can be retrieved based on the tissue code and optionally such that the relation between the tissue code and the tissue is restored based on the quantitative properties being linked with the tissue code, and optionally retrieving the quantitative properties based on the tissue code.

19. Method according to claim 18 further comprising the steps of:
    0) detecting a unique rack code of a rack (R) by means of a further detecting means (100),
    6) placing the tissue on the rack (R),
    7) automatically linking the tissue code with the rack code by means of the processing and storing unit (22), and
    8) automatically storing the so linked codes by way of the processing and storing unit (22) such that the tissue code(s) and thus the respectively linked quantitative properties can be retrieved based on the rack code.

20. Method according to claim 19 further comprising the step of processing the tissues on the rack (R).

21. Method according to claim 20, wherein processing the tissues comprises the steps of Fixation,
Dehydration,
Clearing, and
Impregnation and/or infiltration.

22. Method according to claim 19, wherein steps 1 to 8 are repeated for a plurality of tissues such that the tissue codes can be retrieved based on the rack code.

23. Method according to claim 20, wherein the method further comprises the steps of automatically linking process parameters of the tissue processing with the rack code and also with the tissue code(s), and of storing the so linked process parameters and code(s) such that the process parameters can be retrieved based on the code(s).

* * * * *